United States Patent [19]

Rasberger

[11] 4,380,676
[45] Apr. 19, 1983

[54] PROCESS FOR THE PRODUCTION OF 2,2′-DIHYDROXY-BIPHENYLS

[75] Inventor: Michael Rasberger, Riehen, Switzerland

[73] Assignee: Ciba-Geigy Corporation, Ardsley, N.Y.

[21] Appl. No.: 236,467

[22] Filed: Feb. 20, 1981

[30] Foreign Application Priority Data

Feb. 29, 1980 [CH] Switzerland .................. 1625/80

[51] Int. Cl.³ .................. C07C 39/12; C07C 39/15
[52] U.S. Cl. .................. 568/730; 568/722; 568/723
[58] Field of Search .................. 568/730, 722, 723

[56] References Cited

U.S. PATENT DOCUMENTS

| | | | |
|---|---|---|---|
| 2,490,282 | 12/1949 | Seubold et al. | 568/730 |
| 2,785,188 | 3/1957 | Coe | 260/396 |
| 2,885,444 | 5/1959 | Fookes | 568/730 |
| 3,153,098 | 10/1964 | Boage | 568/730 |
| 3,247,262 | 4/1966 | Kaeding | 568/730 |
| 4,097,461 | 6/1978 | Rutledge | 568/730 |
| 4,238,627 | 12/1980 | Reichle | 568/730 |

FOREIGN PATENT DOCUMENTS

| | | | |
|---|---|---|---|
| 2653188 | 6/1977 | Fed. Rep. of Germany | 568/730 |
| 2332252 | 6/1977 | France | 568/730 |

OTHER PUBLICATIONS

Patai, "The Chemistry of the Hydroxy Group", Part 1, (1971), Interscience Publishers, NY pp. 539–567.

*Primary Examiner*—Werren B. Lone
*Attorney, Agent, or Firm*—Harry Falber

[57] ABSTRACT

A process for the production of 2,2′-dihydroxy-biphenyls of the formula I

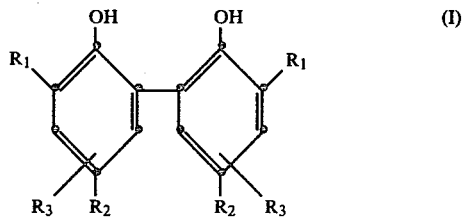

wherein the symbols are as defined in claim 1. The process consists in the oxidative coupling of a phenol of the formula II

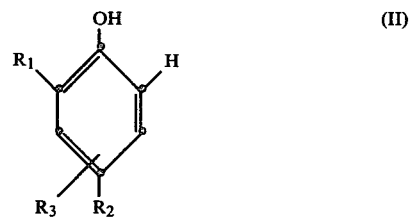

in the presence of a strong inorganic base, with hydrogen peroxide as oxidizing agent. The reaction temperature is in the range from 30° to 100° C. and 1.5 to 4 moles of a base are employed per mole of phenol of the formula II.

11 Claims, No Drawings

PROCESS FOR THE PRODUCTION OF 2,2'-DIHYDROXY-BIPHENYLS

The present invention relates to a novel process for the production of 2,2'-dihydroxy-biphenyls. It is known to obtain 2,2'-dihydroxy-biphenyls from the corresponding phenols by oxidative coupling. The oxidative coupling of phenols with oxygen is described e.g. in U.S. Pat. No. 2,885,444, but the product is only obtained in good yield and in a short reaction time by using a technical phenol in the presence of high concentrations of alkali. The reaction is difficult to control and the results are poorly reproducible. In addition, the product can only be isolated after the addition of acids. Moreover, the use of oxygen in the presence of organic solvents is dangerous on account of the possible formation of explosive mixtures. Air was therefore substituted for oxygen, but in this event the process is only of interest if carried out in the presence of catalysts such as copper powder (U.S. Pat. No. 2,785,188), copper salts (U.S. Pat. No. 3,247,262), or copper, cobalt, manganese or chromium complexes of diketones or keto esters (U.S. Pat. No. 4,097,461).

The action of hydrogen peroxide on oxidative coupling reactions of phenols has also been investigated. Westerfeld et al., Journal of Biological Chemistry 145, 463 (1942), found that the oxidation of phenols with hydrogen peroxide can be catalyzed by peroxidase. However, the main product resulting from the coupling of p-cresol is 2-oxo-4a,8-dimethyl-1,2,4a,9b-tetrahydrodibenzofurane, whereas the desired 2,2'-dihydroxy-5,5'-dimethylbiphenyl is obtained only in less than 5% yield, based on p-cresol.

A process has now been found which permits the oxidative coupling of phenols with hydrogen peroxide.

Accordingly, the present invention provides a process for the production of 2,2'-dihydroxy-biphenyls of the formula I

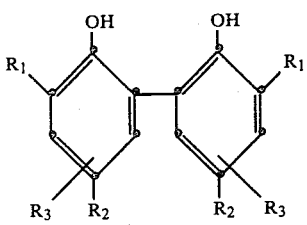

(I)

wherein each of $R_1$ and $R_2$ independently is hydrogen, $C_1$–$C_{18}$alkyl, $C_2$–$C_6$alkenyl, or $C_5$–$C_7$cycloalkyl, phenyl or $C_7$–$C_9$phenylalkyl, each of which is unsubstituted or substituted by one to three $C_1$–$C_4$alkyl radicals, or $R_1$ and $R_3$ together are a butadi-1,3-enyl-1,4-ene radical which is bonded to the benzene ring in the 3,4 and 3',4'-positions, and $R_2$ is also a —(CH$_2$)$_n$COOR$_4$ group, wherein $R_4$ is $C_1$–$C_{18}$alkyl and n is 0, 1 or 2, and $R_3$ is hydrogen or $C_1$–$C_{18}$alkyl, or if $R_1$ is hydrogen, $R_2$ and $R_3$ are a 1,1,3,3-tetramethylpropylene radical which is bonded to the benzene ring in the 4,5- and 4',5'-positions, which process comprises oxidatively coupling a phenol of the formula II

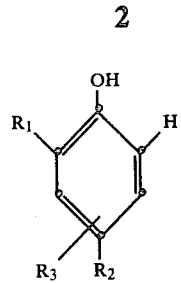

(II)

wherein $R_1$, $R_2$ and $R_3$ are as defined above, with hydrogen peroxide in the presence of a strong inorganic base.

$R_1$, $R_2$, $R_3$ and $R_4$ as $C_1$–$C_{18}$alkyl are straight-chain or branched alkyl radicals such as methyl, ethyl, isopropyl, n-butyl, n-hexyl, 2-ethylhexyl, n-decyl, 1,1,3,3,5,5-hexamethylhexyl, n-tetradecyl or n-octadecyl. In particular, they are $C_1$–$C_{18}$alkyl radicals such as methyl, ethyl, n-propyl, isopropyl, sec-butyl, tert-butyl, tert-amyl or 1,1,3,3-tetramethylbutyl. In preferred phenols of the formula II, $R_1$ is α-branched. In especially preferred phenols of the formula II, $R_1$ and $R_2$ have the same meaning, e.g. tert-butyl or 1,1,3,3-tetramethylbutyl, and $R_3$ is hydrogen. $R_1$ and $R_2$ as $C_5$–$C_7$cycloalkyl which may be substituted by 1 to 3 alkyl groups can be cyclopentyl, o-methylcyclopentyl, p-butylcyclohexyl, 2,4,6-trimethylcyclohexyl, cyclohexyl, cycloheptyl, 1-methylcyclohexyl or m-ethylcyclohexyl. Cyclohexyl is preferred. $R_1$ and $R_2$ as $C_2$–$C_6$alkenyl are e.g. vinyl, allyl, 2-butenyl or 2-hexenyl.

$R_1$ and $R_2$ as phenyl which may be substituted by 1 to 3 $C_1$–$C_4$alkyl groups are e.g. 2,4-dimethylphenyl, 4-butylphenyl, 2,4,6-triethylphenyl and, preferably, phenyl.

$R_1$ and $R_2$ as phenylalkyl which may be substituted by 1 to 3 $C_1$–$C_4$alkyl groups are e.g. o-methylbenzyl, p-butylbenzyl, 2-phenylethyl, benzyl or, preferably, α,α-dimethylbenzyl.

In preferred compounds, $R_3$ is hydrogen and at least one of $R_1$ and $R_2$ is different from hydrogen.

Preferred compounds which can be obtained by the process of the present invention are those of the formula I, wherein $R_1$ and $R_2$ are hydrogen, $C_1$–$C_{18}$alkyl, cyclohexyl, phenyl or α,α-dimethylbenzyl, and $R_3$ is hydrogen or, if $R_1$ is hydrogen, $R_2$ and $R_3$ together are a 1,1,3,3-tetramethylpropylene radical which is bonded to the benzene ring in the 4,5- and 4',5'-positions.

Particularly important compounds obtained by the process of this invention are those of the formula I, wherein one of $R_1$ and $R_2$ is $C_1$–$C_8$alkyl and the other is hydrogen or $C_1$–$C_8$alkyl and $R_3$ is hydrogen.

Examples of phenols of the formula II are: phenol, 2-methylphenol, 2,4-dimethylphenol, 2,4-di-tert-butylphenol, 2-methyl-4-tert-butylphenol, 2-tert-butyl-4-methylphenol, 2,4-di-tert-amylphenol, 2-isopropyl-4-tert-butylphenol, 2-tert-butyl-3-ethyl-4-methylphenol, 2,5-dimethyl-4-tert-butylphenol, 2,4-di-(1',1',3',3'-tetramethylbutyl)-phenol, 2,4,5-trimethylphenol, 4-nonylphenol, 4-dodecylphenol, 2-tert-butyl-4-(1',1',3',3'-tetramethyl)phenol, 2-(1',1',3',3'-tetramethyl)phenol, 2-cyclohexylphenol, 2-phenyl-4-tert-butylphenol, 2-benzylphenol, 2-(o-methylcyclohexyl)phenol or 1,1,3,3-tetramethyl-5-hydroxy-2,3-dihydroindole.

The reaction proceeds almost quantitatively in the temperature range from 30° to 100° C. The reaction times are very short and are less than 5 hours in the temperature range from 50° to 90° C. The reaction can be carried out under a pressure in the range up to 30 atmos.; but in the simplest, and therefore preferred, embodiment, the reaction is carried out at normal pressure.

The technical importance of the novel process resides not least in the fact that relatively small amounts of inorganic base are employed. It has been found that 1.5 to 4 moles, preferably 1.8 to 3 moles, most preferably 2 moles, of an inorganic base, based on 1 mole of phenol of the formula II, suffice to obtain good results in large-scale production. Larger amounts of base are, of course, also possible, but for ecological reasons it is very important to avoid using large amounts of base. Suitable strong inorganic bases are, in particular, hydroxides and carbonates of alkali metals and alkaline earth metals. It is preferred to use sodium or potassium hydroxide.

The process of the invention is advantageously conducted in a solvent. Particularly suitable solvents are water or $C_1$–$C_4$alcohols such as methanol, ethanol, isopropanol or butanol, or mixtures thereof with each other or with water. Other suitable solvents are hydrocarbons such as hexane, benzene or toluene; chlorinated hydrocarbons such as chloroform, chlorobenzene or dichlorobenzene; and amides such as dimethyl formamide or dimethyl acetamide. It is preferred to carry out the process in as concentrated solutions as possible in order to obtain the desired high space-time yields.

The usual procedure is that a ready prepared mixture of base and phenol in the solvent is heated to the reaction temperature and then hydrogen peroxide is added dropwise. Commercially available aqueous solutions of $H_2O_2$ which contain 30 to 126% by volume of hydrogen peroxide are ordinarily employed. In practice, stoichiometric amounts of hydrogen peroxide are employed, so that the volume of the reaction mixture does not increase too greatly. An excess of $H_2O_2$ can also be present in the reaction medium.

A further advantage of these relatively concentrated solutions is that the contact with the phenol is rapid and intensive, resulting in good space-time yields which cannot be obtained with gaseous oxidising agents.

It is known to add surface-active substances to reactions of this kind, especially in order to effect better dispersion of solid substances, but also to simplify the cleansing of the reaction vessels. Surface-active substances (dispersants, surfactants) are organic compounds which contain both hydrophobic and hydrophilic groups in one molecule. Such compounds are described e.g. in Kirk-Othmer, Encyclopedia of Chemical Technology, 2nd edition, Vol. 19, pp. 508–509. All the compounds mentioned therein can be employed in the process of this invention. The concentration in which they are used is not critical and can be e.g. 0.0002 to 0.4 mole per mole of phenol. The use of sodium lauryl sulfate is especially advantageous.

The compounds of the formula I are known intermediates for obtaining, inter alia, antioxidants or flame retardants for plastics.

The invention is illustrated by the following Examples.

EXAMPLE 1

40 g (1 mole) of sodium hydroxide are dissolved in 170 ml of water which contains 1 g of sodium lauryl sulfate. With stirring, the solution is heated to 80° and then 103 g (0.5 mole) of 2,4-di-tert-butylphenol are added. Then 31 ml of a 30% solution of hydrogen peroxide are added dropwise in the course of 2 hours. After the reaction mixture has cooled, the product is isolated by filtration and washed with water and dried, affording 100.5 g (98% of theory) of 2,2'-dihydroxy-3,3',5,5'-tetra-tert-butyl-biphenyl with a melting point of 190°–195° C.

EXAMPLES 2 to 13

The following compounds are obtained in similar manner:

(2) 2,2-dihydroxy-3,3',5,5'-tetra-tert-amylbiphenyl (m.p. 95° C.)

(3) 2,2'-dihydroxy-3,3',5,5'-tetra-(1,1,3,3-tetramethyl-butyl)-biphenyl (m.p. 145° C.)

(4) 2,2'-dihydroxy-3,3'-di-tert-butyl-5,5'-diisopropyl-biphenyl (oil, $C_{calc.}$ 81.6, $C_{found}$ 81.2; $H_{calc.}$ 10.01, $H_{found}$ 10.00)

(5) 2,2'-dihydroxy-3,3'-di-tert-butyl-5,5'-di-(1,1,3,3-tetramethylbutyl)-biphenyl (oil, $C_{calc.}$ 82.69, $C_{found}$ 82.2; $H_{calc.}$ 11.18, $H_{found}$ 11.00)

(6) 1,1,3,3-tetramethyl-5-hydroxy-6-(1', 1', 3',3'-tetramethyl-5-hydroxy-indan-6'-yl)-indane (7) 2,2'-dihydroxy-3,3'-di-tert-butyl-5,5'-octadecyloxy-propionyl-biphenyl (8) 2,2'-dihydroxy-3,3'-di-tert-butyl-5,5'-dinonyl-biphenyl (9) 2,2'-dihydroxy-3,3'-di-vinyl-5,5'-di-tert-butyl-biphenyl

(10) 2,2'-dihydroxy-3,3'-diphenyl-5,5'-dimethyl-biphenyl

(11) 2,2'-dihydroxy-3,3'-dicyclohexyl-5,5-di-tert-butyl-biphenyl

(12) 2,2'-dihydroxy-3,3'-di-tert-butyl-5,5'-dimethyl-biphenyl

(13) 2-(1'-hydroxy-4'-tert-butyl-2'-naphthol)

What is claimed is:

1. A process for the production of a 2,2'-dihydroxybiphenyl of the formula I

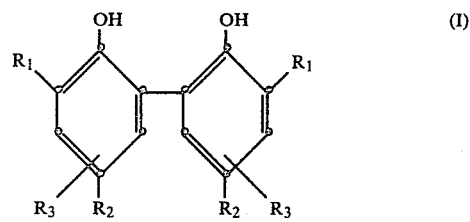

wherein each of $R_1$ and $R_2$ independently is hydrogen, $C_1$–$C_{18}$alkyl, $C_2$–$C_6$alkenyl, or $C_5$–$C_7$cycloalkyl, phenyl or $C_7$–$C_9$phenylalkyl, each of which is unsubstituted or substituted by one to three $C_1$–$C_4$alkyl radicals, or $R_1$ and $R_3$ together are a butadi-1,3-enyl-1,4-ene radical which is bonded to the benzene ring in the 3,4 and 3', 4'-positions, and $R_2$ is also a —$(CH_2)_n COOR_4$ group, wherein $R_4$ is $C_1$–$C_{18}$alkyl and n is 0, 1 or 2, and $R_3$ is hydrogen or $C_1$–$C_{18}$alkyl, with the proviso that when $R_1$ is hydrogen, $R_2$ and $R_3$ are a 1,1,3,3-tetramethylpropylene radical which is bonded to the benzene ring in the 4,5- and 4',5'-positions, which process comprises oxidatively coupling, at elevated temperatures, a phenol of the formula II

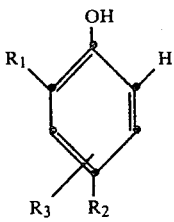 (II)

wherein $R_1$, $R_2$ and $R_3$ are as defined above, with hydrogen peroxide in the presence of a strong inorganic base.

2. A process according to claim 1, wherein $R_1$ and $R_2$ are hydrogen, $C_1$-$C_{18}$alkyl, cyclohexyl, phenyl or $\alpha,\alpha$-dimethylbenzyl, and $R_3$ is hydrogen, with the proviso that when $R_1$ is hydrogen, $R_2$ and $R_3$ together are a 1,1,3,3-tetramethylpropylene radical which is bonded to the benzene ring in the 4,5- and 4',5'-positions.

3. A process according to claim 1, wherein one of $R_1$ and $R_2$ in formula I is $C_1$-$C_{18}$alkyl and the other is hydrogen or $C_1$-$C_8$alkyl and $R_3$ is hydrogen.

4. A process according to claim 1, wherein the reaction is carried out in the temperature range from 30° to 100° C.

5. A process according to claim 1, wherein the strong inorganic base is a hydroxide or carbonate of an alkali metal or alkaline earth metal.

6. A process according to claim 1, wherein 1.5 to 4 moles of a strong inorganic base are employed, based on the phenol of the formula II.

7. A process according to claim 1, wherein the process is carried out in a solvent.

8. A process according to claim 7, wherein the reaction is carried out in water or a $C_1$-$C_{14}$alcohol, or in a mixture of such alcohols with each other or with water.

9. A process according to claim 1, wherein the hydrogen peroxide is employed in the form of an aqueous solution containing 30 to 126% by volume of $H_2O_2$.

10. A process according to claim 1, wherein the reaction is carried out in the presence of a surface-active compound.

11. A process according to claim 10, wherein the reaction is carried out in the presence of sodium lauryl sulfate.

* * * * *